United States Patent [19]

Essen-Moller

[11] Patent Number: 5,657,759
[45] Date of Patent: Aug. 19, 1997

[54] MEASUREMENT OF GASTRIC EMPTYING AND GASTROINTESTINAL OUTPUT

[75] Inventor: Anders Essen-Moller, Stockholm, Sweden

[73] Assignee: Synectics Medical, Incorporated, Irving, Tex.

[21] Appl. No.: 369,552

[22] Filed: Jan. 6, 1995

Related U.S. Application Data

[63] Continuation of Ser. No. 60,931, May 13, 1993, abandoned.

[51] Int. Cl.$^6$ ....................................................... A61B 6/00
[52] U.S. Cl. ............................ 128/654; 128/656; 128/658
[58] Field of Search .................................. 128/653.1, 654, 128/656, 658, 659, 774, 780, 631, 635, 670, 671, 736; 364/413.02, 413.13, 413.26; 604/264, 268, 280

[56] References Cited

U.S. PATENT DOCUMENTS

| | | |
|---|---|---|
| 2,162,656 | 6/1939 | Warrington . |
| 2,168,867 | 8/1939 | George, III ............................. 128/635 |
| 2,857,915 | 10/1958 | Sheridan . |

(List continued on next page.)

FOREIGN PATENT DOCUMENTS

| | | |
|---|---|---|
| 0073558 | 3/1983 | European Pat. Off. . |
| 0080680 | 6/1983 | European Pat. Off. . |
| 0241644 | 10/1987 | European Pat. Off. . |
| 356603 | 11/1993 | European Pat. Off. . |
| 0356603 | 11/1993 | European Pat. Off. . |
| 2162656 | 6/1973 | Germany . |
| 2453630 | 11/1980 | Germany . |
| 3140265 | 4/1983 | Germany . |
| 221635 | 5/1985 | Germany . |
| 3523987 | 1/1987 | Germany . |
| 7707275 | 1/1979 | Netherlands . |
| 178028 | 11/1966 | U.S.S.R. . |
| 272477 | 5/1968 | U.S.S.R. . |
| 1502004 | 8/1989 | U.S.S.R. . |

OTHER PUBLICATIONS

Maycock et al., "A Long Term Remote Intragastric pH and Motility Monitoring System", Bio–Med Sciences Instrumentation 6th National Symposium, May 21–23, 1968, pp. 127–133.

"Clinical relevance of ambulatory 24–hour . . . ", Vogten, et al., 1987, pp. 21–31 in Netherlands Journal of Medicine.

"Computerized Axial Manometry of the Esophagus", Bombeck, et al. in Annals of Surgery, vol. 206, No. 4, pp. 465–472, Oct. 1987.

"The laser motility sensor for long–term study of intra–esophageal pressure", Schneider et al., in Primary Motility Disorder of the Esophagus, Giuli et al., eds., pp. 64–69 1991.

Kim et al., American Journal of Clinical Pathology, 1990, vol. 94, pp. 187–191, "The Gastric Juice Urea and Ammonia . . . ".

(List continued on next page.)

Primary Examiner—Brian L. Casler
Attorney, Agent, or Firm—Stephen C. Glazier

[57] ABSTRACT

A system and a method for evaluation of gastrointestinal function is presented. The system consists of a catheter, a recorder and software. The catheter includes one or more CdTe sensors for measuring isotope activity. The catheter CdTe sensors are placed in the gastrointestinal tract to measure gastric emptying or gastrointestinal output after administration of radiolabeled liquid or solid meals. Data is stored in the recorder or displayed online on a computer screen. Other parameters such as pH can be added for a more complete evaluation of gastrointestinal function. The computer software is written for the Windows environment. The software includes provisions for general ambulatory and stationary data acquisition. The software also includes real-time analysis combined with an extensive patient journal where all items are described as objects in understandable userfriendly language connected to a database. With the present invention it is for the first time made possible to study gastrointestinal output and gastric emptying on an ambulatory basis.

7 Claims, 19 Drawing Sheets

U.S. PATENT DOCUMENTS

| | | | |
|---|---|---|---|
| 3,373,735 | 3/1968 | Gallagher . | |
| 3,480,003 | 11/1969 | Crites . | |
| 3,669,095 | 6/1972 | Kobayashi et al. | 128/659 |
| 3,690,309 | 9/1972 | Pluzhnikov et al. | 128/631 |
| 3,817,241 | 6/1974 | Grausz . | |
| 3,905,889 | 9/1975 | Macur et al. . | |
| 3,923,626 | 12/1975 | Niedrach et al. . | |
| 4,016,866 | 4/1977 | Lawton . | |
| 4,063,548 | 12/1977 | Klatt et al. . | |
| 4,073,287 | 2/1978 | Bradley et al. . | |
| 4,119,498 | 10/1978 | Edwall et al. . | |
| 4,176,659 | 12/1979 | Rolfe . | |
| 4,197,852 | 4/1980 | Schindler et al. . | |
| 4,208,588 | 6/1980 | Rudin | 600/5 |
| 4,214,593 | 7/1980 | Imbruce et al. . | |
| 4,265,249 | 5/1981 | Schindler et al. . | |
| 4,299,929 | 11/1981 | Sakano et al. . | |
| 4,381,011 | 4/1983 | Somers, 3rd . | |
| 4,442,841 | 4/1984 | Uehara et al. . | |
| 4,471,779 | 9/1984 | Antoshkiw et al. . | |
| 4,476,871 | 10/1984 | Hon . | |
| 4,478,222 | 10/1984 | Koning et al. . | |
| 4,486,290 | 12/1984 | Cahalan et al. . | |
| 4,487,206 | 12/1984 | Aagard . | |
| 4,503,859 | 3/1985 | Petty et al. . | |
| 4,508,103 | 4/1985 | Calisi . | |
| 4,577,640 | 3/1986 | Hofmeister . | |
| 4,593,701 | 6/1986 | Kobayashi et al. . | |
| 4,595,014 | 6/1986 | Barrett et al. | 128/654 |
| 4,600,015 | 7/1986 | Evans et al. . | |
| 4,618,929 | 10/1986 | Miller et al. . | |
| 4,631,061 | 12/1986 | Martin . | |
| 4,632,119 | 12/1986 | Reichstein . | |
| 4,642,104 | 2/1987 | Sakamoto et al. . | |
| 4,655,225 | 4/1987 | Dahne et al. . | |
| 4,681,116 | 7/1987 | Settler . | |
| 4,682,596 | 7/1987 | Bales et al. . | |
| 4,691,708 | 9/1987 | Kane . | |
| 4,696,672 | 9/1987 | Mochizuki et al. . | |
| 4,700,709 | 10/1987 | Kraig . | |
| 4,700,799 | 10/1987 | Kawano . | |
| 4,703,757 | 11/1987 | Cohen . | |
| 4,705,503 | 11/1987 | Dorman et al. . | |
| 4,729,384 | 3/1988 | Bazenet . | |
| 4,748,113 | 5/1988 | Marshall . | |
| 4,748,562 | 5/1988 | Miller et al. . | |
| 4,757,194 | 7/1988 | Simms . | |
| 4,776,347 | 10/1988 | Matthews . | |
| 4,796,629 | 1/1989 | Grayzel . | |
| 4,803,992 | 2/1989 | Lemelson . | |
| 4,815,471 | 3/1989 | Stobie . | |
| 4,834,101 | 5/1989 | Collison et al. . | |
| 4,850,371 | 7/1989 | Broadhurst et al. . | |
| 4,873,990 | 10/1989 | Holmes et al. . | |
| 4,887,610 | 12/1989 | Mittal . | |
| 4,892,101 | 1/1990 | Cheung et al. . | |
| 4,901,731 | 2/1990 | Millar . | |
| 4,924,877 | 5/1990 | Brooks . | |
| 4,966,161 | 10/1990 | Wallace et al. . | |
| 4,975,581 | 12/1990 | Robinson et al. . | |
| 4,976,265 | 12/1990 | Falcial et al. . | |
| 4,981,470 | 1/1991 | Bombeck, IV . | |
| 4,986,671 | 1/1991 | Sun et al. . | |
| 4,991,590 | 2/1991 | Shi . | |
| 4,996,161 | 2/1991 | Conners et al. . | |
| 5,005,584 | 4/1991 | Little . | |
| 5,007,427 | 4/1991 | Suzuki et al. | 128/659 |
| 5,018,529 | 5/1991 | Tenerz . | |
| 5,022,396 | 6/1991 | Watanabe . | |
| 5,025,786 | 6/1991 | Siegel . | |
| 5,046,497 | 9/1991 | Millar . | |
| 5,047,627 | 9/1991 | Yim et al. . | |
| 5,054,487 | 10/1991 | Clarke . | |
| 5,103,835 | 4/1992 | Yamada et al. . | |
| 5,105,812 | 4/1992 | Corman . | |
| 5,108,364 | 4/1992 | Takezawa et al. . | |
| 5,117,827 | 6/1992 | Stuebe et al. . | |
| 5,119,498 | 6/1992 | McNeill et al. . | |
| 5,151,598 | 9/1992 | Denen | 128/654 |
| 5,158,083 | 10/1992 | Sacristan et al. . | |
| 5,184,619 | 2/1993 | Austin . | |
| 5,199,443 | 4/1993 | Maurer et al. . | |
| 5,207,226 | 5/1993 | Bailin et al. . | |
| 5,222,594 | 6/1993 | Sumino . | |
| 5,280,786 | 1/1994 | Wlodarczyk et al. . | |
| 5,291,884 | 3/1994 | Heinemann et al. . | |
| 5,301,673 | 4/1994 | Rabito et al. | 128/659 |
| 5,314,804 | 5/1994 | Boguslaski et al. . | |

OTHER PUBLICATIONS

Butcher et al., Digestion, 1992, vol. 53, pp. 142–148, "Use of an Ammonia Electrode for Rapid Quantification of Helicobacter pylori Urease: Its use in the Endoscopy Room and in the . . . ".

The New Yorker, Sep. 20, 1993, T. Monmaney, "Marhsall's Hunch".

"Oesophageal multipurpose monitoring probe", Baker et al., Anaesthesia, 1983, vol. 38, pp. 892–897.

Digestive Diseases, Reprint, vol. 8, Suppl. 1, pp. 60–70, 1990, Scarpignato et al., "Simultaneous Measurement and Recording . . . ".

Hojgaard et al., "A New Method for Measurement of the Electrical Potential Difference Across the Somach Wall", 1991. pp. 847–858.

"Ambulatory Monitoring of Gastric Emptying", Hoeft et al., May 16 1993, American Assoc. of the Study of Live Diseases.

MEASUREMENT OF GASTRIC EMPTYING AND GASTROINTESTINAL OUTPUT

This is a continuation of application Ser. No. 08/060,931, filed May 13, 1993, abandoned.

FIELD OF INVENTION

The present invention relates to a system consisting of an analysis software package, a digital data acquisition recorder, a sensor catheter and a method for evaluation of gastrointestinal function. More particularly, the present invention relates to a system and a method to measure gastric emptying or gastrointestinal output.

Specifically the system can be used on a stationary and/or an ambulatory basis by placing a miniature gamma counter (including one or more isotope sensitive elements such as a cadmium-tellurium (CdTe) crystal) transnasally into the stomach or other part of the gastrointestinal tract of a patient. Said sensors register how markers, such as in a radiolabeled liquid or a solid meal, decline or are passing by in a given time. By connecting said miniature gamma counter to a preamplifier and a combined stationary and ambulatory data acquisition recorder, gastric emptying or gastrointestinal output can be measured and data stored. During or after the procedure data is transferred into an IBM compatible personal computer where said data is analyzed, compared to normal and presented in various forms with dedicated software.

Gastric emptying has not previously been measured by an intragastrointestinal catheter. Nor has gastric emptying previously been measured on an ambulatory basis. Unlike cardiac output (that is, the amount of blood that the heart pumps out to the aorta per time unit), gastrointestinal output have not previously been thought of as a parameter of interest. The present invention therefor represents a significant improvement to the arsenal of available methods for accessing gastrointestinal function.

In addition to said measurements of isotope activity the present invention includes the possibility to measure other parameters simultaneously such a bile, pH, EGG, IGG and pressure in order to better assess gastrointestinal function and correlate various parameters with disease.

BACKGROUND

Gastric motor function such as propulsion of grounded chymous into the small bowel is difficult to assess. Several methods have been employed, in the prior art, including dye dilution which requires intubation of the stomach and duodenum, radiographic studies using barium salts, and more recently developed techniques with ultrasonic and applied potential tomography equipment (Mangnall 1989). The best prior art method of assessing gastric emptying at present is, however, the use of radionuclide-labeled meals (Fisher 1990).

Gastric Emptying. With the prior art, gastric emptying of radiolabeled solids and liquids can be evaluated simultaneously when the various phases are marked with different tracers such as 99mTc and 111In respectively. Frequently used radiolabeled solid and liquid meals include chicken liver, eggs, oatmeal, orange juice and water. After ingestion of a labeled meal, anterior and posterior gamma camera images of the stomach area are obtained in 5 to 15 minute intervals for 1.5 to 2.0 hours. After correction for decay, the counts in the gastric area are plotted as percentages of total counts at the start of imaging. Results are often presented as curves of emptying for liquids or solids against time, with the 5th and 95th percentiles of normals for comparison. A simpler technique of assessment is to derive the T1/2, which is the time taken to empty 50% of a meal from the stomach. These prior art methods are performed with the patient immobilized over a relatively short time period (e.g., 2 hours) and are far from the physiological environment associated with meals.

The present invention is a system and a method for gastric emptying and gastrointestinal output using an intragastrointestinal catheter which can be used on both stationary and ambulatory basis and represents therefor a significant advantage over prior art. As compared with today's prior art method of choice, the present invention does not use an expensive external gamma camera. In addition the present invention uses an intragastrointestinal catheter reducing the amount of radiolabeled material needed. Furthermore, the present invention enables ambulatory procedures which allows for a more physiologic environment when the meals are ingested and processed.

Prior art catheters that include sensors for isotope activity have been used to assess gastroduodenal reflux of radiolabeled bile (Stoker 1990) but not gastric emptying nor gastrointestinal output from any region of the gastrointestinal tract. Ambulatory data acquisition recorders are well known for assessing 24 hour pH and pressure from various parts of the gastrointestinal tract, but monitoring gastric emptying or output on an ambulatory basis in a physiological environment in the clinic or in the patient's home has not previously been taught.

It is an object of the present invention to provide a stationary and ambulatory system with which gastric emptying and gastrointestinal output from any part of the gastrointestinal tract can be assessed. It is a further object of the present invention that patients undergoing a gastric emptying test with radiolabeled liquids and solids shall be able to take their meals in as normal circumstances as possible. It is yet a further object of the present invention that the amount of ingested radiolabeled material can be reduced as compared with present stationary gamma counters. It is yet a further object of the present invention to enable simultaneous measurement of said radiolabeled material with other parameters such as pH, bile, EGG, IGG and pressure. It is yet a further object of the present invention to present a unique software data acquisition program for recording, analysis and reporting gastric emptying and intragastrointestinal output procedures, said program also including provisions for defining and carrying out other procedures of the gastrointestinal tract, said program also including provisions for including results of said procedures in a patient journal database system.

Other methods with which this invention can be compared include stationary gastric emptying (as opposed to gastric output) studies in which radiolabeled liquids or solid meals are administered to a patient in and which the patient is positioned under a external gamma-camera which registers the declining isotope activity from the stomach as the stomach empties its contents. Unlike the present invention such methods are performed under unphysiological conditions, offer no means for ambulatory measurement of gastric emptying or output, offer no means for placing the sensor directly in the flow stream of the material to be measured, and offer no means for measurement of other parameters on a simultaneous basis.

SUMMARY OF THE INVENTION

The present invention describes a system and a method that includes an intragastrointestinal isotope activity sensor catheter, a combined stationary and ambulatory recorder and a dedicated software program. Said catheter includes a tubular body and one or more isotope activity sensors. Other sensors may also be included. The various isotope activity sensors can be used either to measure various isotopes or the same isotope at various positions. Each isotope activity sensor communicates through the interior of the tubular body to the proximal end of the catheter and is used for the purpose of detecting isotope activity. Said catheter is connected to an external preamplifier which is connected to a multichannel digital data acquisition recorder. Said recorder records the number of counters per second as detected by the isotope activity sensors. Other parameters such as pH, pressure, EGG, IGG and bile may be recorded simultaneously. Measured data can be displayed in realtime by means of an on-line interface on a computer screen or stored in the digital memory of the recorder. The digital recorder is previously described in European Patent Application 88850292.9. Stored data is uploaded to an IBM compatible computer. Said dedicated computer software computes, analyses and reports data in graphic and numerical form and compares results to normality. Said software also includes provisions for carrying out other medical procedures and provisions to include results from said and other procedures into a database patient journal system. The present invention includes the method of making the gastric emptying procedures ambulatory by using said system.

Gastrointestinal Output. The present invention also includes a new procedure called "gastrointestinal output". Once the intragastrointestinal isotope activity sensor catheter (possibly including other sensors such as described herein) is properly positioned, it will be connected to an appropriate monitor and recorders of stationary or ambulatory type. The patient will then be given a radiolabeled meal. In the ambulatory case, the patient can walk about as the data for an ambulatory gastric emptying or gastrointestinal output study is being recorded via the isotope activity sensor (and possibly other sensors) in the catheter.

The method of determining gastrointestinal output (which is a new parameter) monitors the isotope activity from a cylindric volume of gastrointestinal contents corresponding to the length of the sensing isotope element. Because the administered isotope amount is known as well as its concentration, by detecting how much isotope activity is passing the detector it is possible to calculate the relative flow in units of volume per time of the ingested meal that the sensor sees and correlate this to gastric output. In this way it is for the first time possible to monitor gastric output in real time.

DETAILED DESCRIPTION OF THE INVENTION

Figure 1:
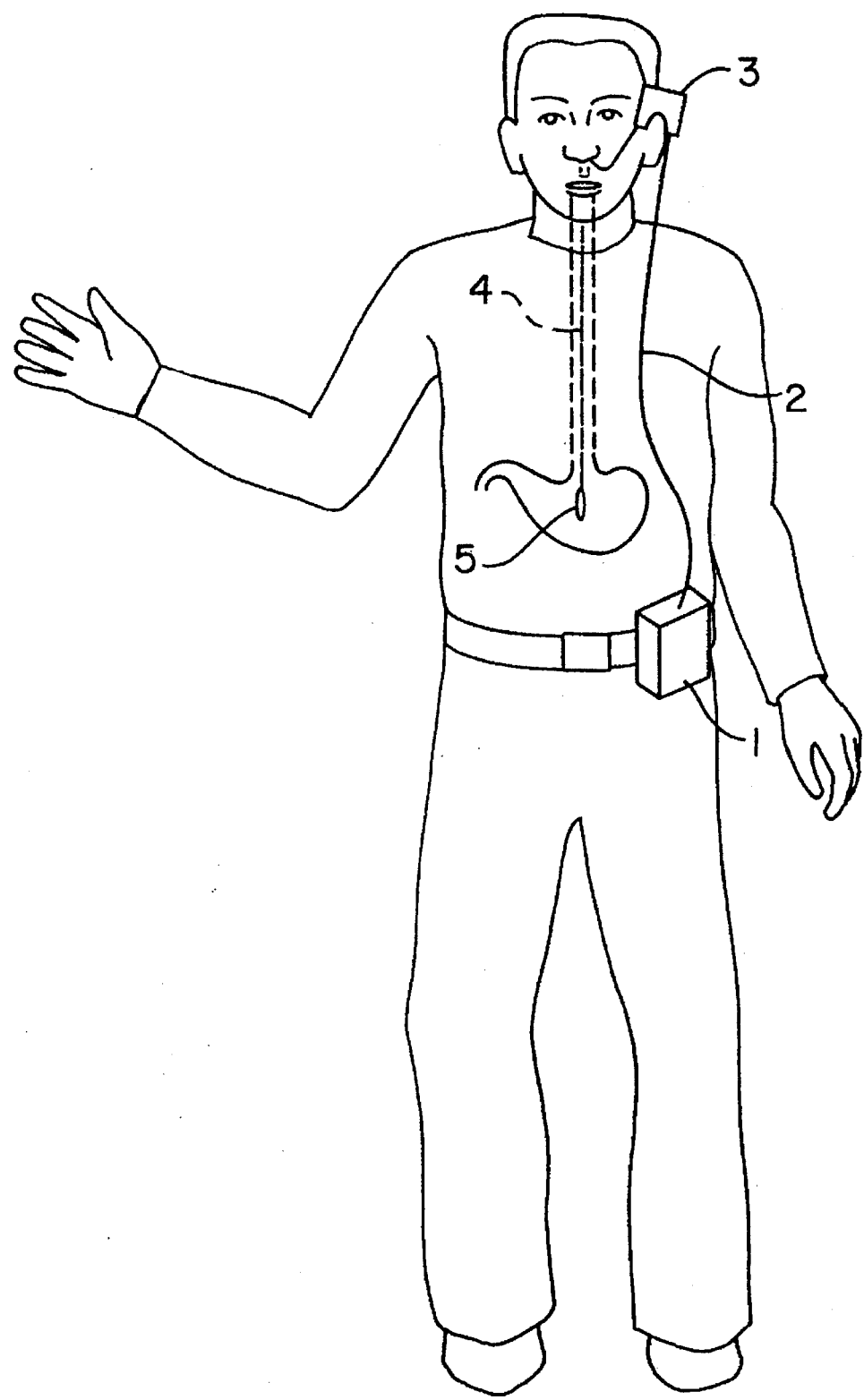
FIG. 1 displays a patient with the intragastric catheter, preamplifier and recorder in accordance with the present invention.

FIG. 1 displays a patient wearing the ambulatory recorder 1 which is connected via a cable 2 to the preamplifier 3 and the intragastrointestinal catheter 4 with its CdTe sensing crystal 5 in the stomach for measurement of gastric emptying.

Figure 2:
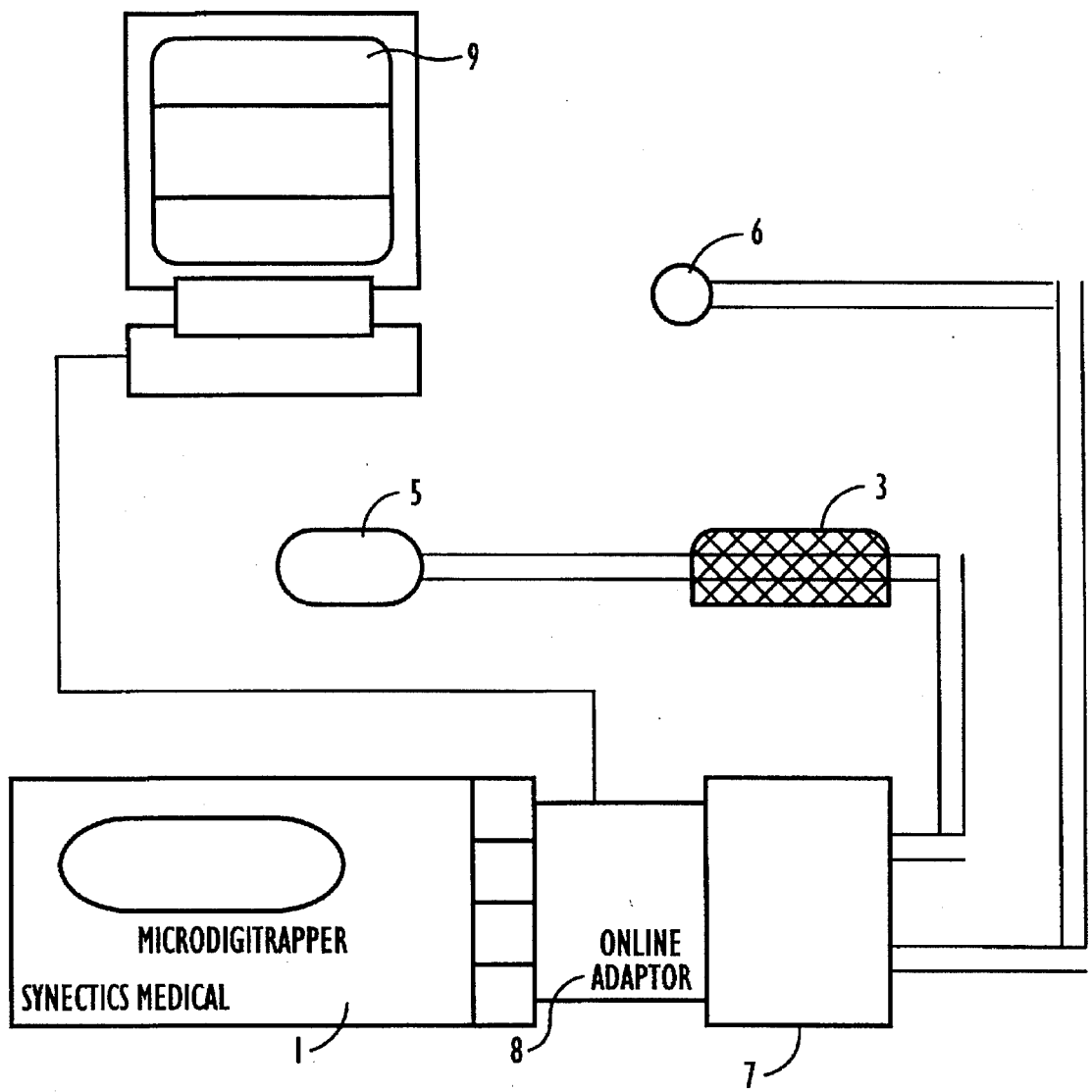
FIG. 2 displays how the isotope sensor, and a pH sensor are connected to the recorder, via an on-line interface, for realtime display on a computer screen in accordance with the present invention.

In FIG. 2 the CdTe sensor 5 and the preamplifier 3 are together with a pH sensor 6 connected to a recorder 1, via a direct current converter with a cascade voltage amplifier 7 and an on-line adaptor 8 for direct realtime online display of recorded data on a computer screen 9.

Figure 3:
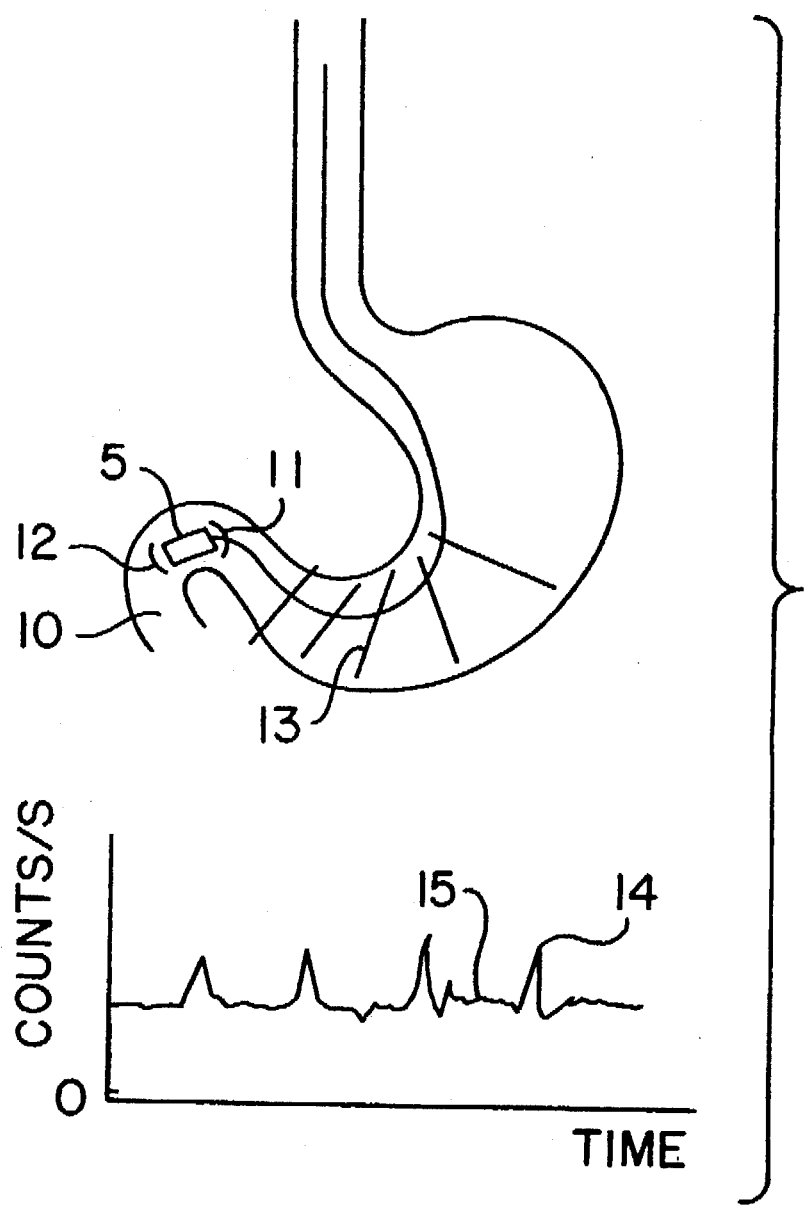
FIG. 3 shows an alternative positioning of the isotope sensitive probe for a gastric output procedure.

FIG. 3 displays an alterative placement of the CdTe isotope activity sensing crystal 5 in the duodenum 10. Shields 11 and 12 at the proximal and distal ends of the crystal 5 minimizes background radiation noise from a radioactive meal in the stomach 13. Gastric output can be recorded as gushes 14 above background 15 as the processed food material passes the crystal 5 often at a frequency of 3 times per minute.

Figure 4:
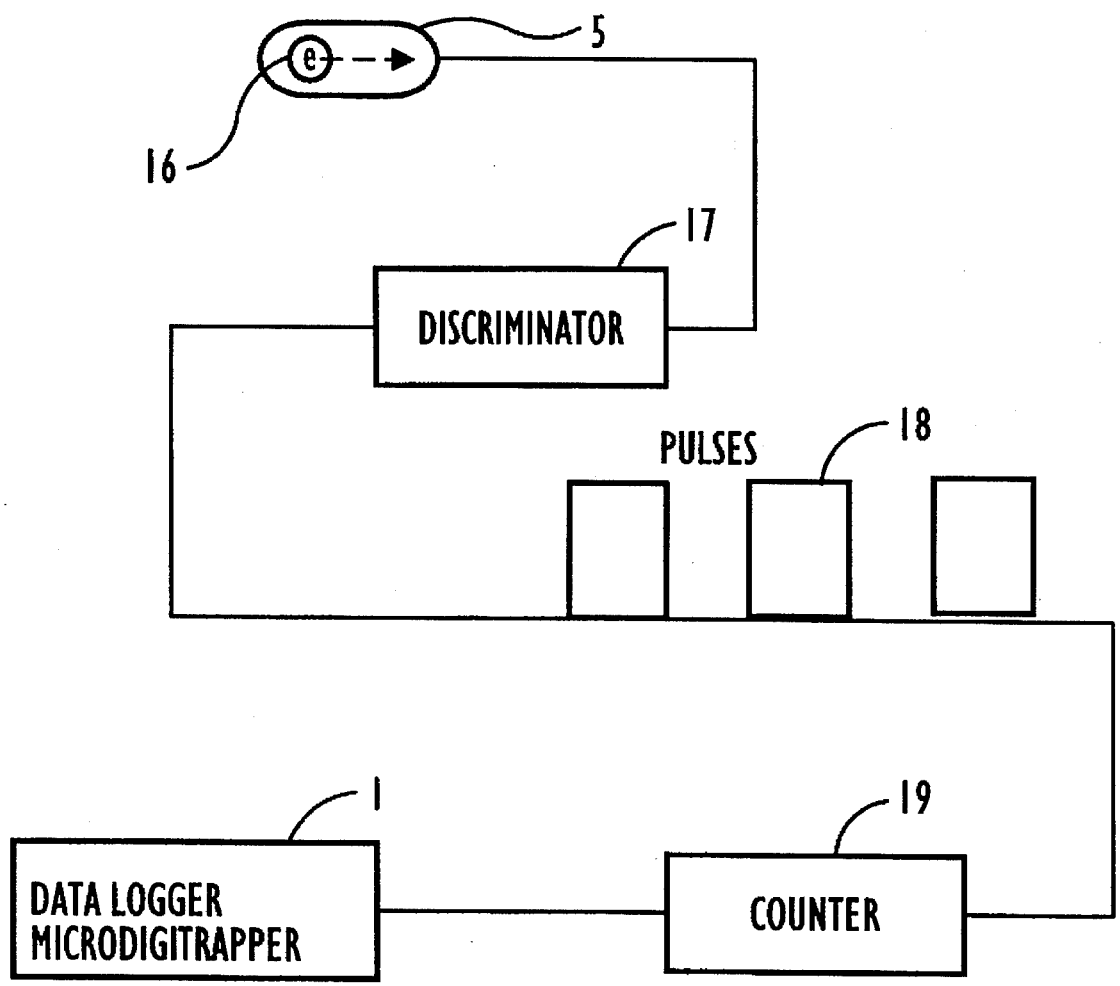
FIG. 4 displays how a photon enters the isotope sensor and generates a pulse that travels via a discriminator and counters to the recorder in accordance with the present invention.

FIG. 4 shows how the CdTe sensor element 5, is impacted by a photon 16 exceeding a certain energy level. Said photon generates an electrical signal which passes to a discriminator 17 where only pulses 18 from certain isotopes pass. Said pulses are then counted in a counter 19 and the counted number stored in the digital recorder 1.

Figure 5:
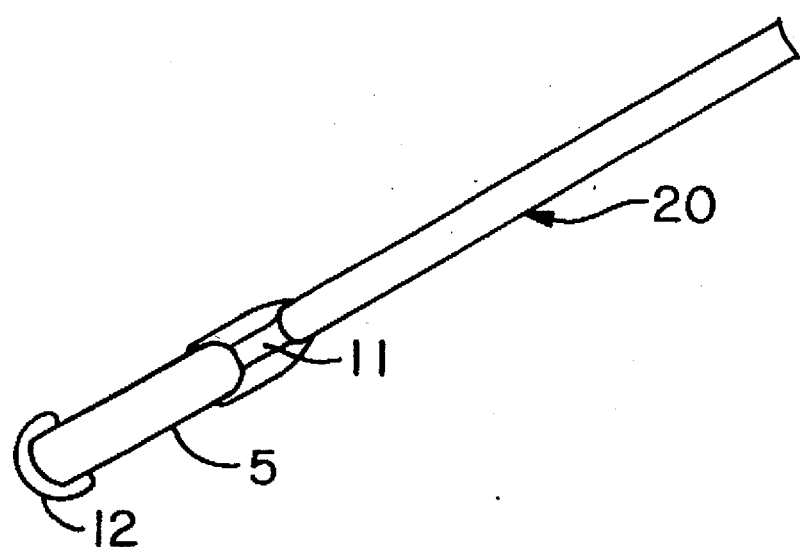
FIG. 5 shows a view of the distal portion of the isotope-catheter with gold shielded proximal and distal ends.

FIG. 5 shows the CdTe sensor element 5 with gold shields 11 and 12 at the proximal and distal ends of said sensor element. Proximal to said sensor is a shielded cable 20 leading to a preamplifier 3.

Figure 15:
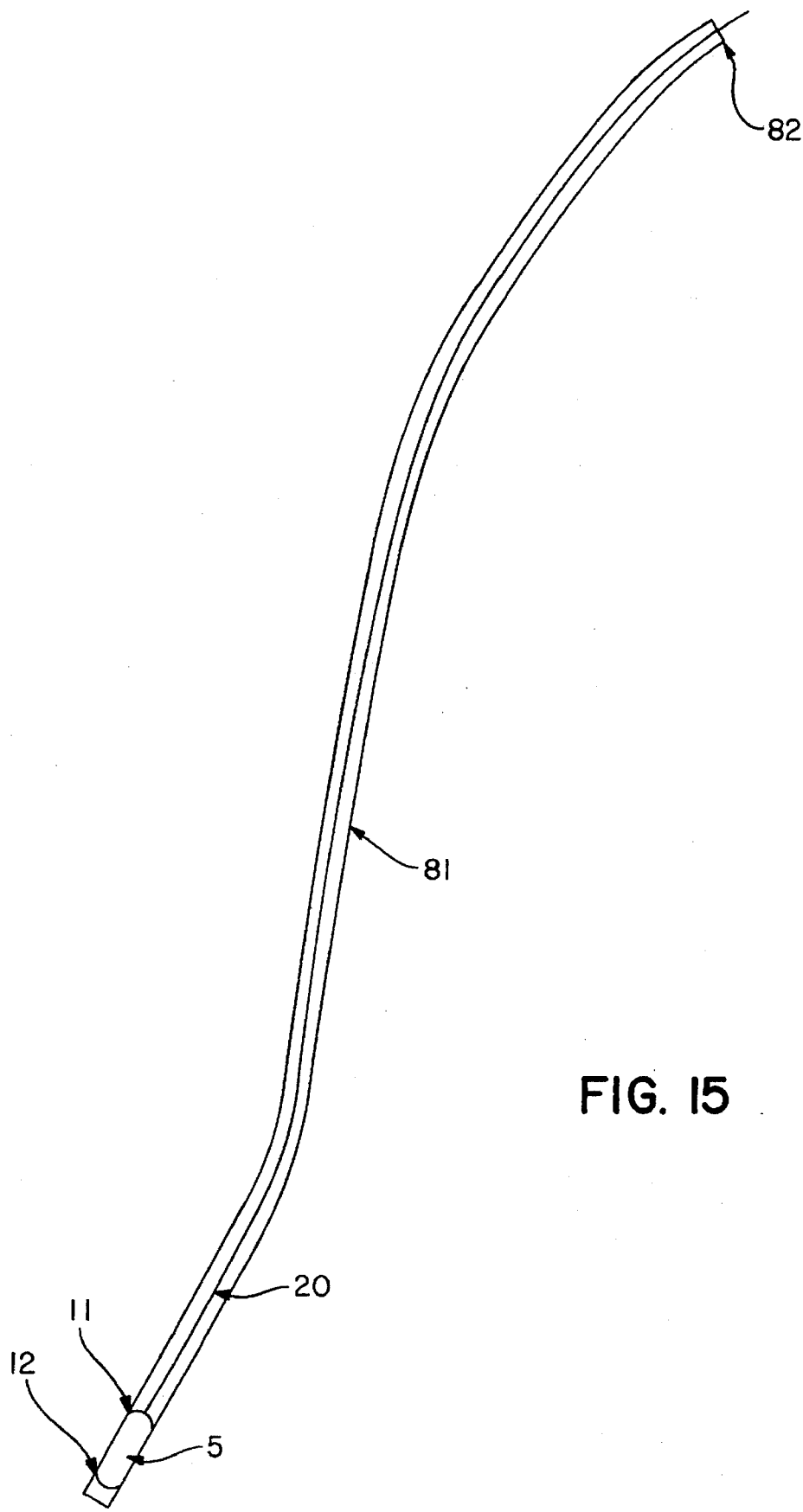
FIG. 15 shows a side view of the same catheter embodiment shown in FIG. 5, but with further elements shown.

FIG. 15 shows a side view of the same catheter embodiment shown in FIG. 5, but with further elements shown. The tubular body 81 with the proximal end 82 of the body 81, are shown. The first isotope activity sensor 5 in the catheter is connected to an electrical conductor 20, which may be a shielded cable, which runs through the interior of the body 81 to the proximal end 82 of the body 81.

Figure 16:
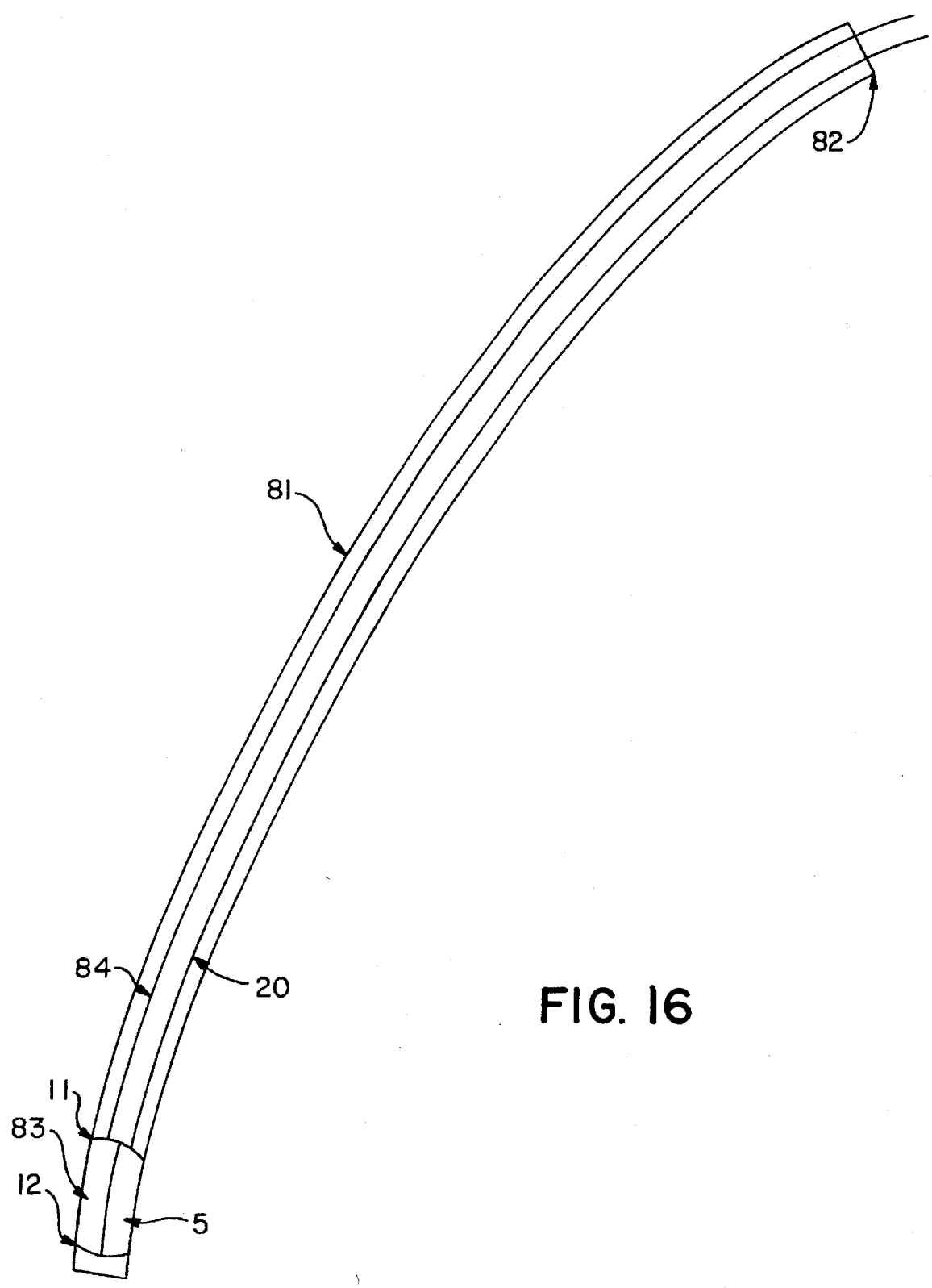
FIG. 16 shows a variation of the catheter embodiment of FIG. 15, with a second isotope sensor.

FIG. 16 shows a variation of the catheter embodiment of FIG. 15, with a second isotope activity sensor 83 in the catheter adjacent to the first sensor 5 and sensing a type of isotope different from the type sensed by the first sensor. The second isotope activity sensor 83 is connected to an electrical conductor 84, which may be a shielded cable, which runs through the interior of the body 81 to the proximal end 82 of the body 81. The second sensor 83 may be located between the same gold shields 11 and 12 as the first sensor 5.

Figure 17:
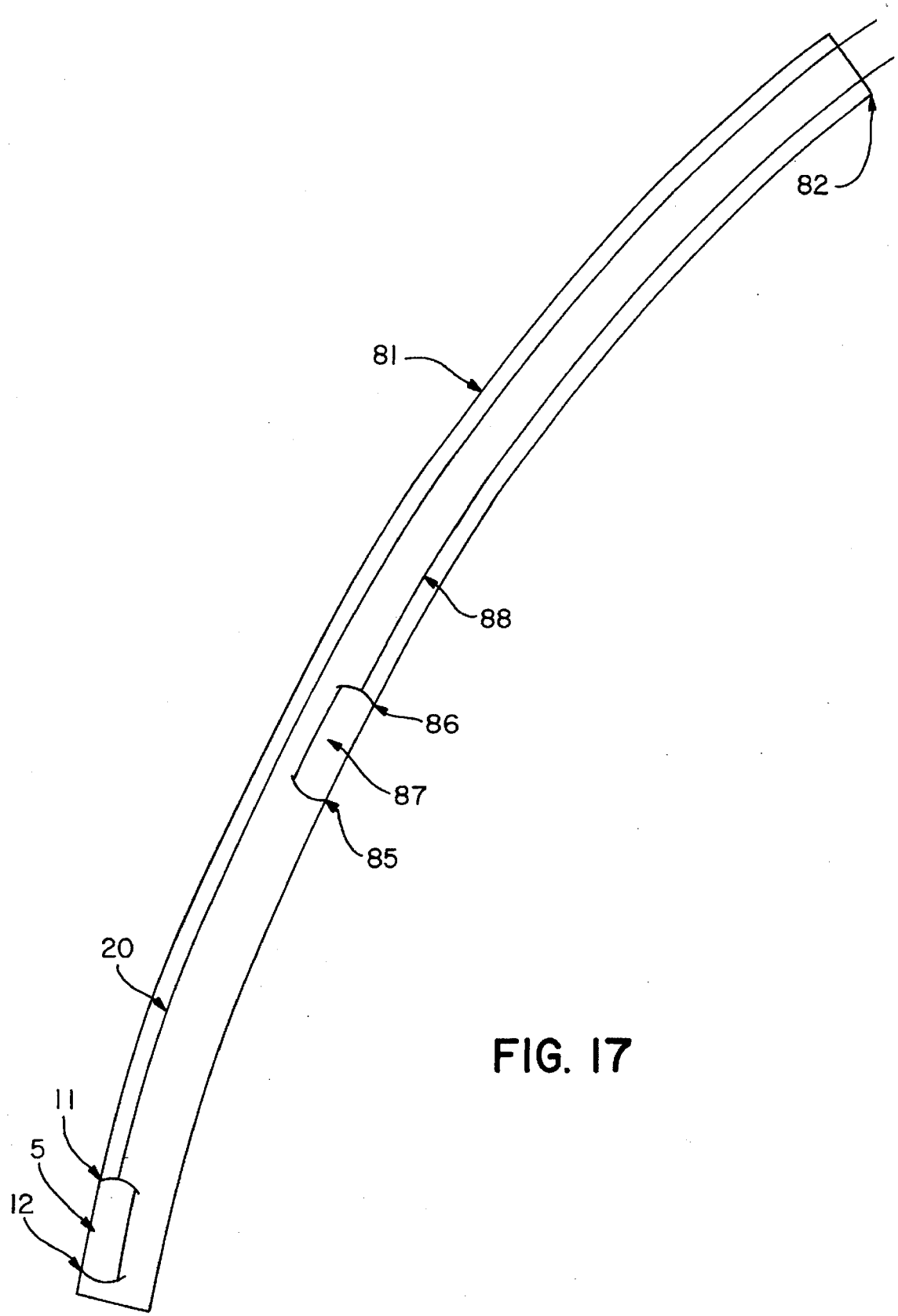
FIG. 17 shows a variation of the catheter embodiment of FIG. 15, with a third isotope sensor.

FIG. 17 shows a variation of the catheter embodiment of FIG. 15, with a third isotope activity sensor 87 in the catheter, at a location on the body 81 not adjacent to the first sensor 5, the third sensor sensing the same isotope type as the first sensor 5. The third sensor 87 may be located between gold shields 85 and 86 at the distal end and proximal end, respectively, of the third sensor 87. The third isotope activity sensor 87 is connected to an electrical conductor 88, which may be a shielded cable, which runs through the interior of the body 81 to the proximal end 82 of the body 81. As shown, this embodiment has no second sensor 83, although it may be used.

Figure 18:
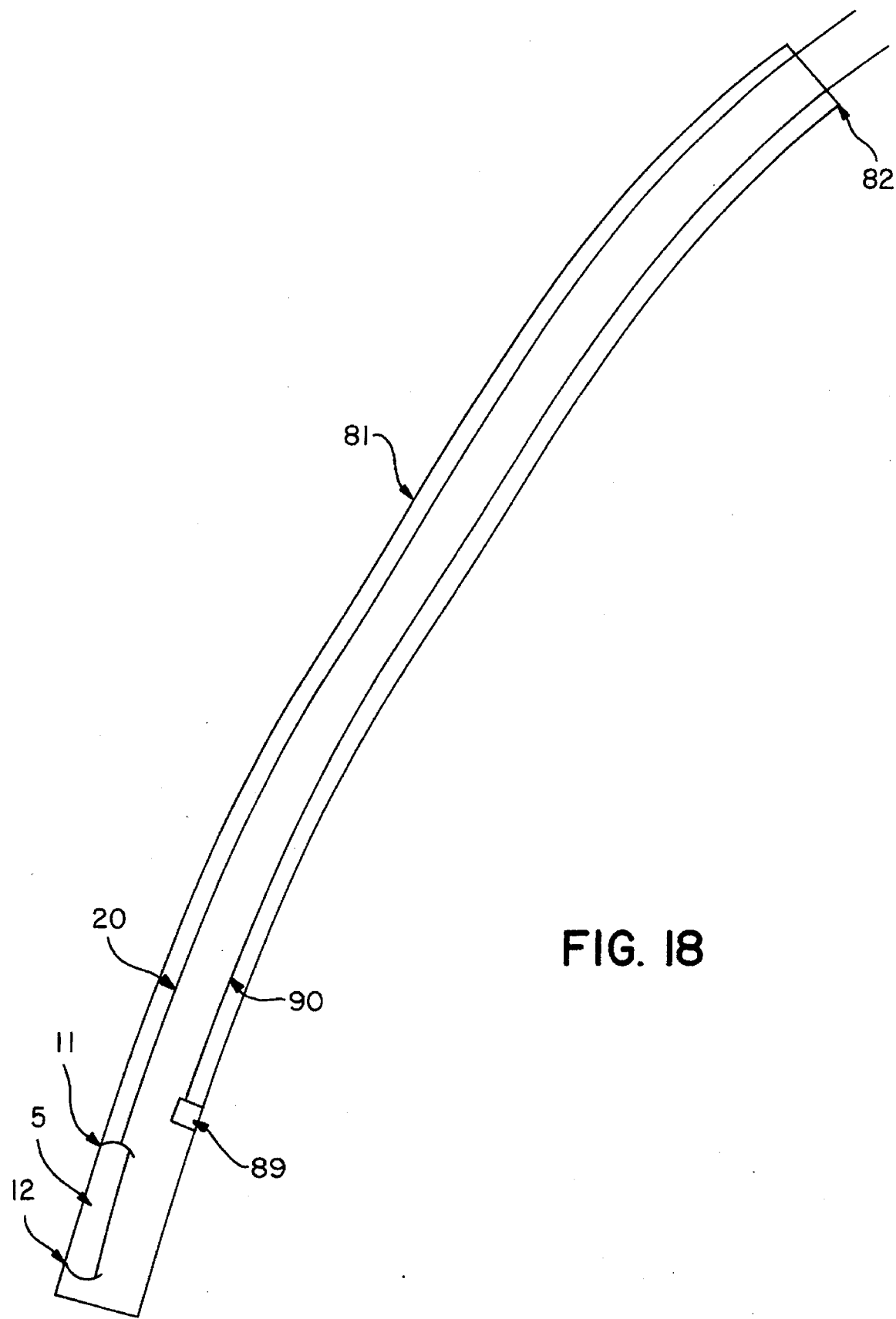
FIG. 18 shows a variation of the catheter embodiment of FIG. 15, with a fourth sensor.

FIG. 18 shows a variation of the catheter embodiment of FIG. 15, with a fourth sensor 89 attached to the catheter. The fourth sensor 89 in a specific embodiment may be one sensor selected from the group of sensors that each sense, respectively, one of the following parameters including pH, impedance, IGG, EGG, pressure, and bile. The fourth sensor 89 is connected to an electrical conductor 90, which may be a shielded cable, which runs through the interior of the body 81 to the proximal end 82 of the body 81. As shown, this embodiment has no second sensor 83 and no third sensor 87, although either or both may be used also.

Figure 19:
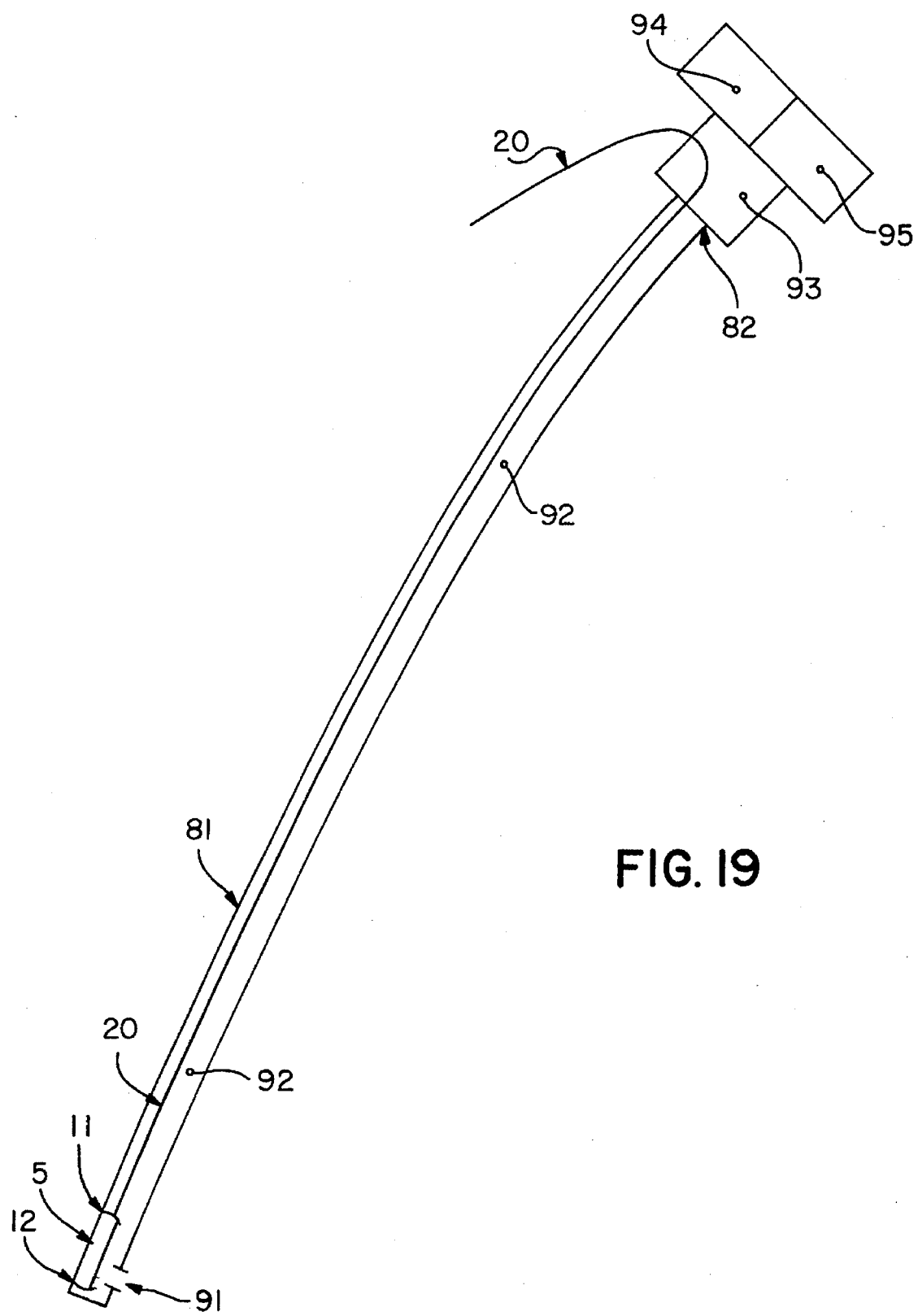
FIG. 19 shows a variation of the catheter embodiment of FIG. 15, with a perfusion lumen in the body of the catheter.

FIG. 19 shows a variation of the catheter embodiment of FIG. 15, with a perfusion lumen 92 in the body 81 of the catheter, and with an outlet hole 91 through the body 81, the hole located at or near the distal end of the body 81. This embodiment is shown with a connector 93 at the proximal end 82 of the body 81. The connector 93 is adapted for connection to a perfusion pump 95 and a pressure transducer 94, so that the pump 95 may pump a fluid through the lumen 92 and out the outlet hole 91 while the pressure of the fluid is measured by the pressured transducer 94. As shown, this embodiment has no second sensor 83, third sensor 87, or fourth sensor 89, although they may be used alone or together in any combination with the first sensor 5 and/or the lumen 92.

Figure 6:
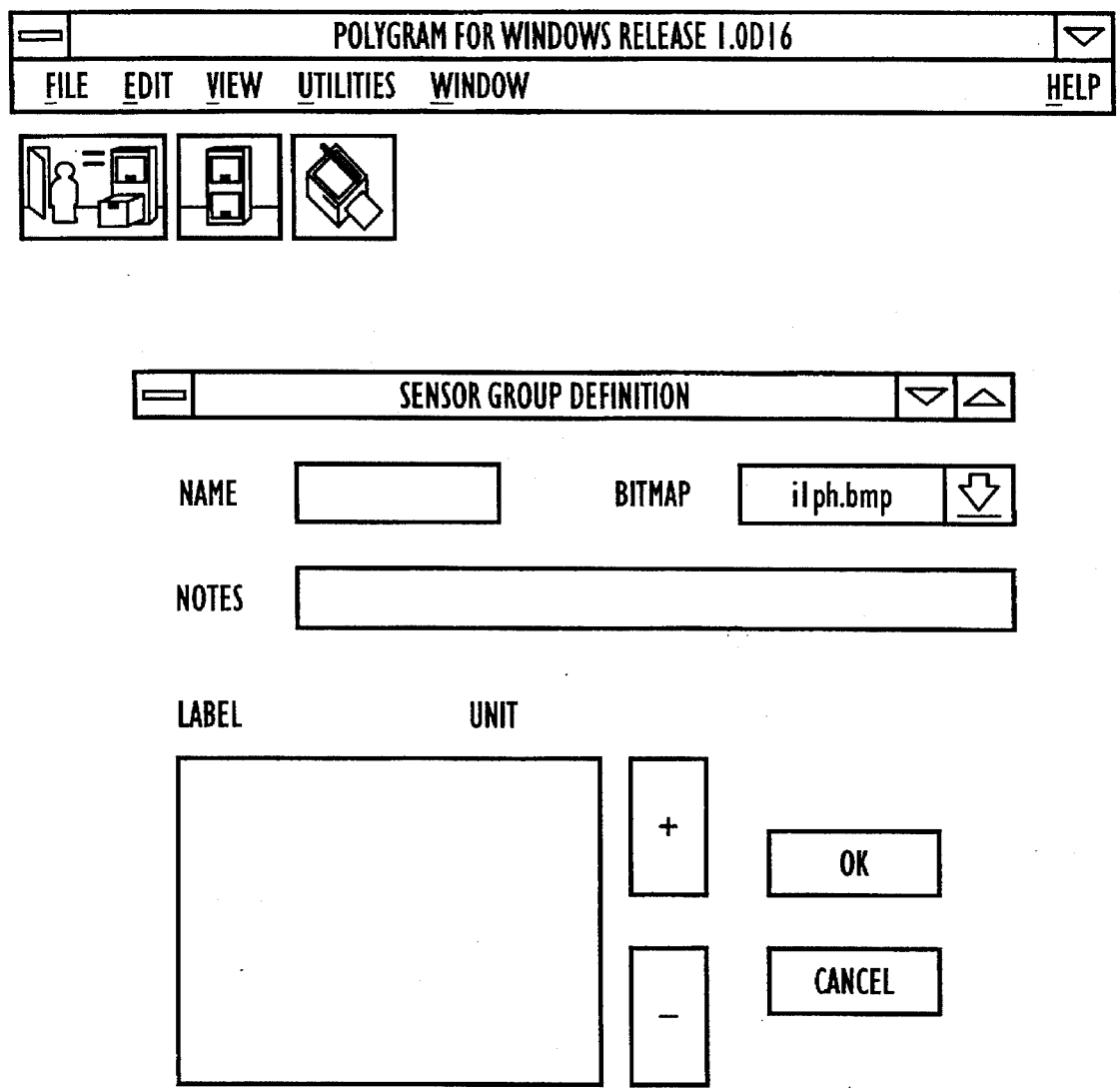
FIG. 6 shows the Sensor Group screen of the software in accordance with the present invention.

A dedicated software package for ambulatory and stationary gastric emptying and gastrointestinal output procedures is written in C++ under the Windows environment. It is designed so that it can be used generally as a software program for patient journals combined with stationary and ambulatory data acquisition, analysis and reports of parameters such as ECG, EMG, pulse, EGG, pH, respiration, $pO_2$, pressure, video and so forth. Its unique design includes an option FIG. 6 under Utilities where various Sensor Groups are designed and stored. A Sensor Group may be a catheter with several different sensors for such measurements as isotope activity, pH, pressure and so forth. The sensors are clearly and userfriendly described as objects using real names as this function is connected to a database. In the Design Sensor Group option it is possible to set such features as distance between sensors, type of sensors, resolutions, possible measurement ranges, and temperature constants.

Figure 7:
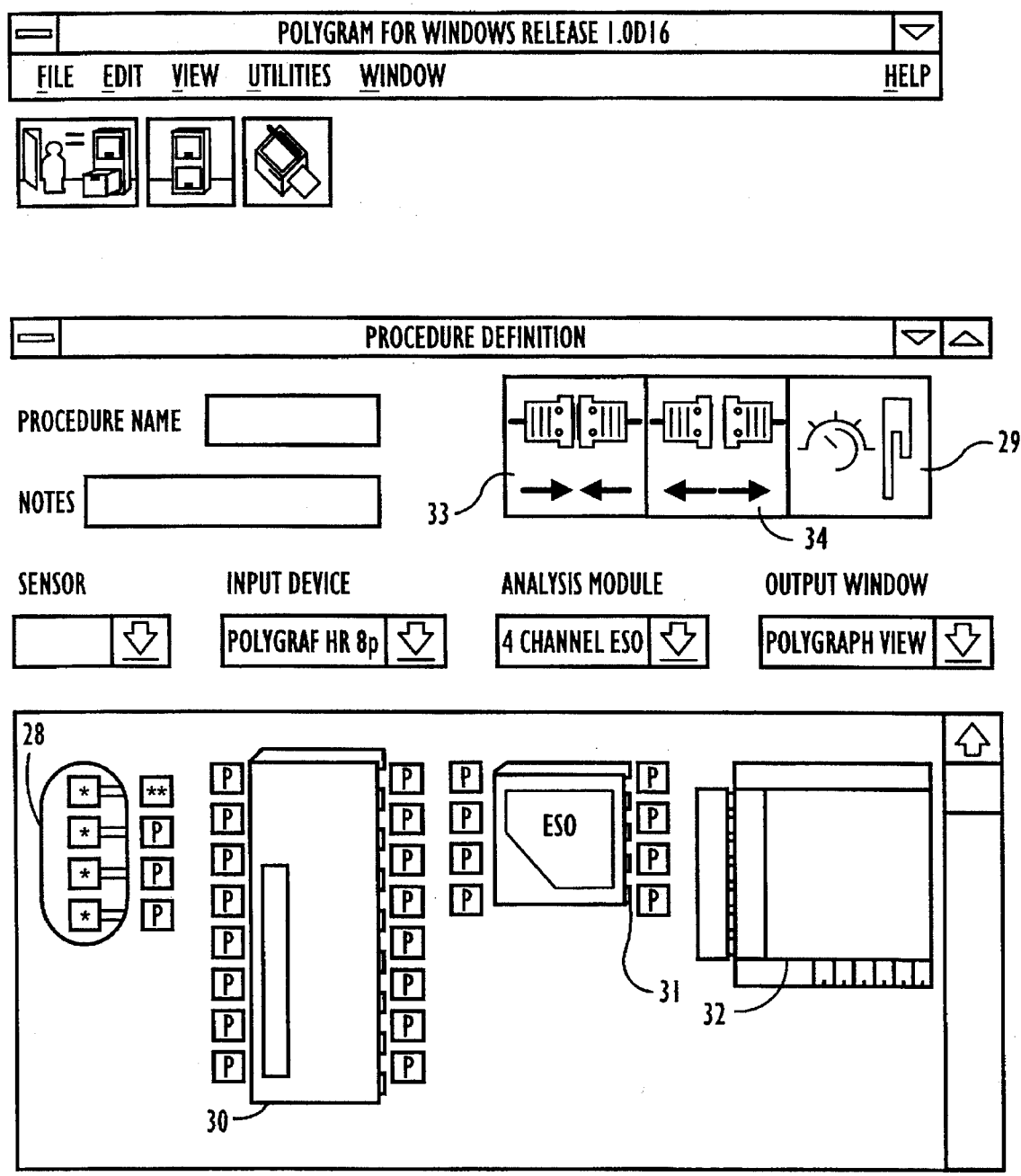
FIG. 7 shows the Procedure screen of the software in accordance with the present invention.

In a similar way also under the Utilities option, it is possible in Procedure Definition option FIG. 7 to describe database connected objects in easy to understand terminology as various acquisition units 30 that shall be used in a procedure. Several such acquisition units of different types can be used simultaneously such as a 16 channel stationary polygraph, an 8 channel ambulatory recorder, and a video recorder. Said several acquisition units can be used simultaneously in a procedure. New hardware data acquisition units can be installed and added to the selection. When defining a procedure, a set of Sensor Groups and an adequate set of hardware data acquisition units are selected. With icon 29, instructions can be given about what markers and buttons shall be available for the user in the particular procedure. Factors such as sampling rates, calibration values and measurement ranges are also set.

Defining a procedure also incudes selecting a realtime analysis module 31 that appropriately manipulates data before it is sent to an output device 32 such as a screen, printer or video recorder, said output devices being installed in Utilities under a separate Add Resources option. As in the application for gastric emptying and gastrointestinal output procedures, the realtime analysis module may correct counted photons for decay before said values are displayed on screen. Calculating the decay-corrected numbers is done with the following formula, $$A_{(corr)} = A_{(act)} * e^{k*t}$$

Where $A_{(corr)}$ is the corrected count, $A_{(act)}$ is the actual count, k is the decay constant $(\ln(2)/t_{(half)}$, and t is the time difference between the actual time and the starting time.

The $t_{(half)}$ time of $^{99m}$ technetium is 6.04 hours. In addition, said real time analysis may perform a fast frequency analysis of the detected gushes of radioactive material that passes the CdTe sensor in the gastrointestinal output study to enable display of the frequency of pyloric relaxation or gastrointestinal contraction. Other realtime analysis functions may be to perform similar fast frequency analysis for measurements such as pressure changes, and pattern gastric depolarization waves.

Icon 33 in FIG. 7 enables the user to autoconnect sensor group 28 with hardware 30, analysis module 31 and output unit 32. Autoconnect basically works so that sensor channel 1 selects the first available adequate hardware channel which is connected to the first adequate analysis channel which is connected to the first free available output channel. With icon 34 on the other hand the user can design the interconnection routes simply by clicking the mouse on a sensor and moving it to a required hardware channel, and so forth. Once designed the procedure is saved as an object connected database item under an understandable name. The fact that objects are connected to a database allows customized userfriendly communication with the program. This is unlike objects that are given file names only, such as in Lab Windows from National Instruments.

Figure 8:
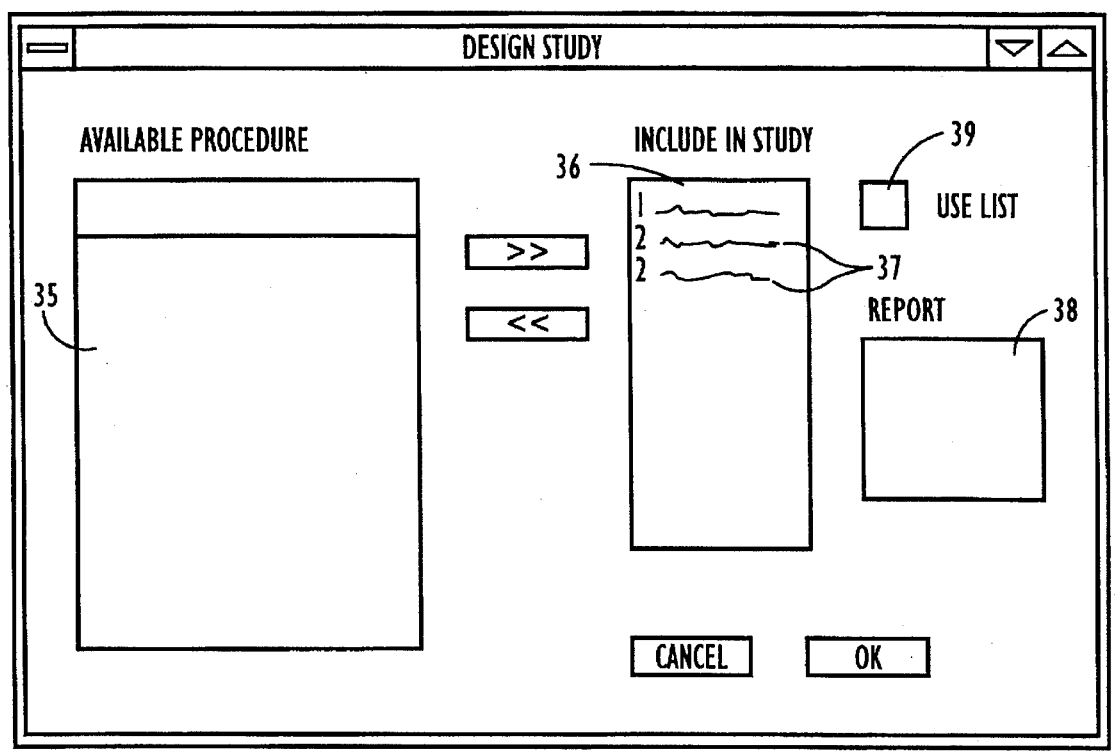
FIG. 8 shows the Study screen of the software in accordance with the present invention.

A Study may include several procedures and is defined under Utilities. For instance a gastric workup study may include a gastric emptying procedure and an antroduodenal motility and pH procedure. In such a case each procedure is defined and stored under the Procedure Definition option. In the Design Study option FIG. 8, available Procedures 35 can be selected that are to be included in a study 36 and carried out in consecutive order. It is possible by holding down the Ctrl key at the same time as a Procedure is being included in the Study list, to add Procedures 37 that are to be carried out simultaneously in two separate windows on the same patient. It is also possible for instance to carry out 8 identical procedures simultaneously in 8 different windows. By connecting various hardware to different patients this feature enables monitoring of several patients in a medical department. The Study is connected to an adequate report including the option to generate a letter to the patient or the referral doctor by clicking in the Report Box 38. By clicking the Use List Box 39 the Report information is channelled to the Patient Journal (see further discussion below).

Figure 9:
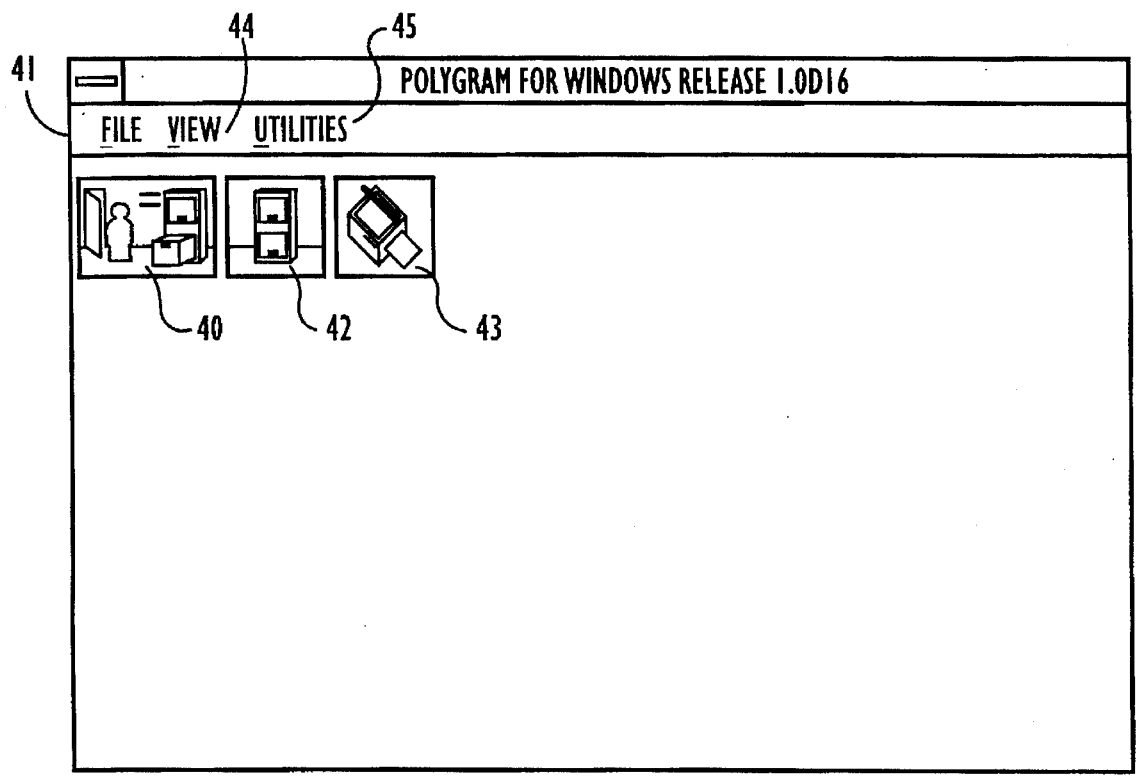
FIG. 9 shows the Opening screen of the software in accordance with the present invention.

FIG. 9 illustrates an initial software screen designed in the Windows environment and in accordance with the present invention. The screen includes icon 40 for patient handling. Unlike the Windows standard for file handling, both the new files (entering new patients) and open files (loading existent patient files) are combined in one icon button and in one combined option (open/new) under Files 41 only. Other initial icons include icon 42 for closing file sand icon 43 for printing purposes.

File 41 includes an option to delete patient files. View 44 includes the option to bring various bars on screen including a realtime instruction bar. Utilities 45 includes options to design Sensor Groups, Procedures Studies and to add Resources.

Figure 10:
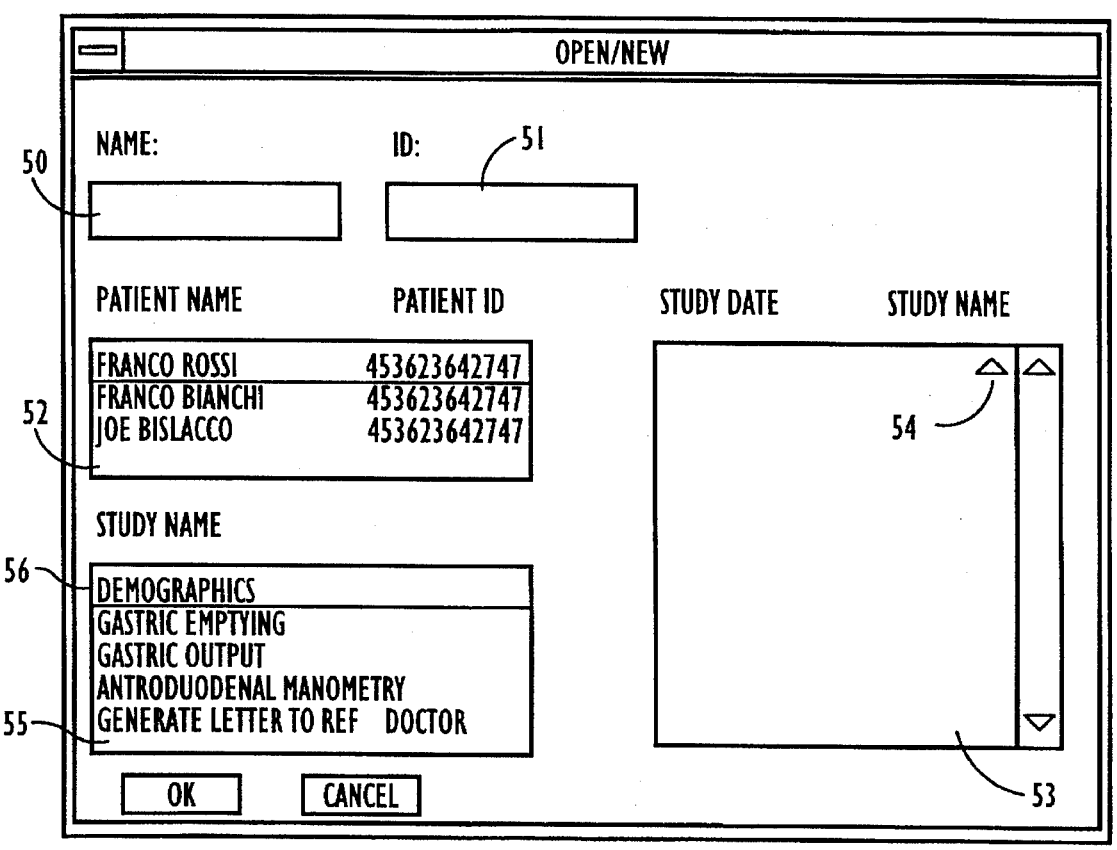
FIG. 10 shows the Patient Selection and Journal screen of the software in accordance with the present invention.

Selecting icon 40 or Open/New from File 41 leads to a screen as in FIG. 10. There is no prior name in the Patient Name 50 and ID 51 boxes. If a new patient is to be registered, the user simply types said patients name and ID into said boxes. Alternatively if an "already existing" patient is to be handled said existing patient can be found in the Patient List box 52. An existing patient is selected by clicking with the Mouse and the name and ID are displayed in the Name and ID boxes. In addition said patient's Patient Journal 53 is displayed to the left. The Patient Journal displays for each default certain dates of interest with a comment such as which procedure was carried out on that date, what was discussed, or if any images were taken. By clicking on a particular date or comment the full report as defined in Design Study is displayed including images and sequences of live video. By clicking on the enlargement button 54 in the next upper right corner, the Patient Journal fills the screen and a third column becomes visible to the right of previous displayed columns. Said third column contains additional detailed comments, similar to said comments, related to the dated events, including options to click on for bringing additional in depth information to the screen.

Said Patient Journal is made easy to handle as each event is described in normal language as an object related to a database. One entry in the database may be the address to a position where live video, or a short particular segment of a polygraph recording is stored. In this way it is possible to build up large patient journal databases where various information is stored at various places, such as on different disks.

If more than one patient is to be monitored at the same time the Ctrl key is pushed while selecting additional patients. Selected patient is highlighted. If more than one patient is selected said patients will be numbered on a consecutive basis as selected. Said numbers will correspond to the corresponding screen number that is created when several procedures are selected simultaneously, such as under the Design Study option.

When several patients are selected the Name 50 and ID 51 boxes become enlarged so that all selected patients are included in said boxes. Similarly the Patient Journal 53 will be tiled in smaller windows so that each patient displays a Patient Journal window.

Figure 11:
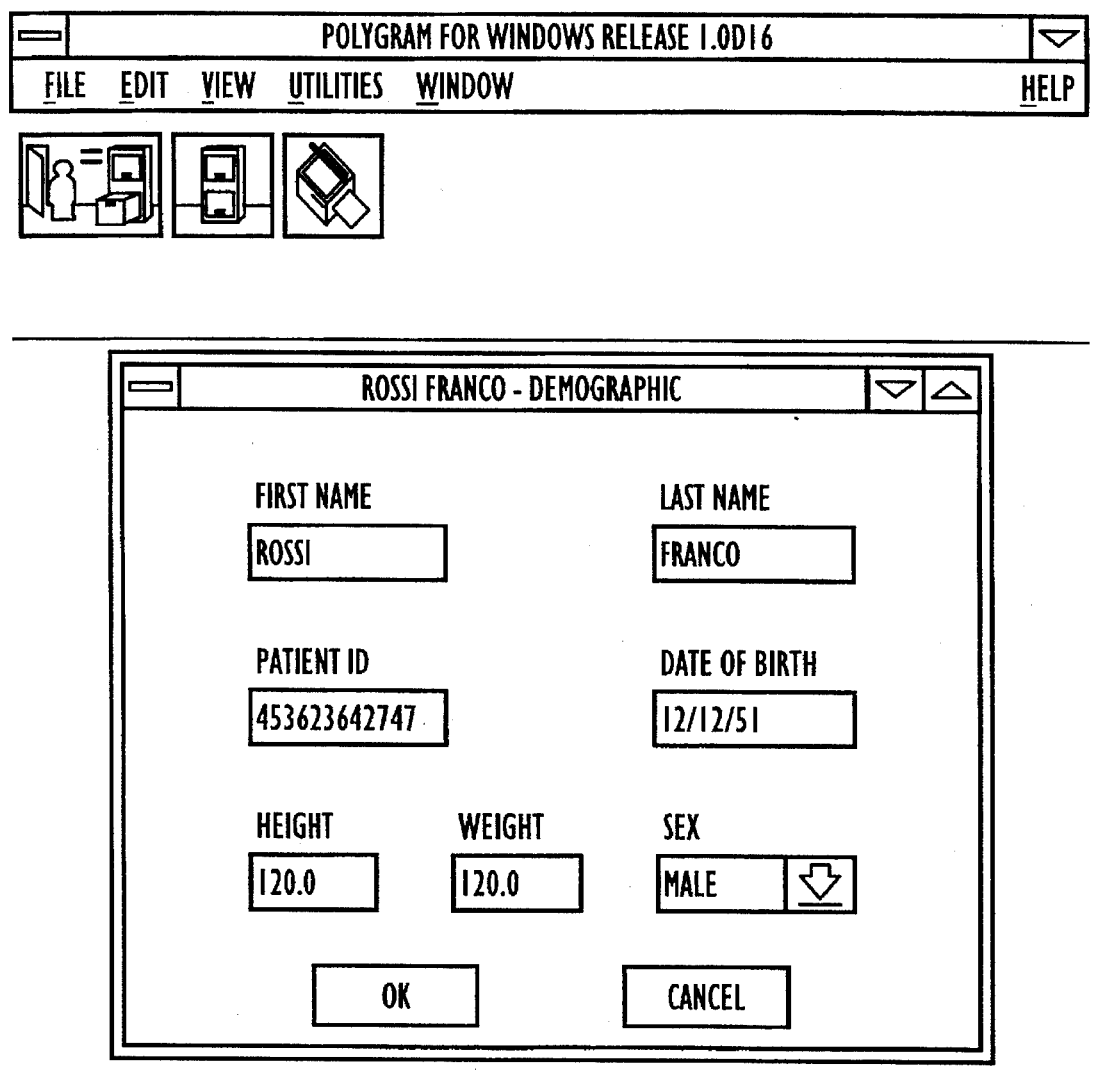
FIG. 11 shows the Patient Registration screen of the software in accordance with the present invention.
Figure 12:
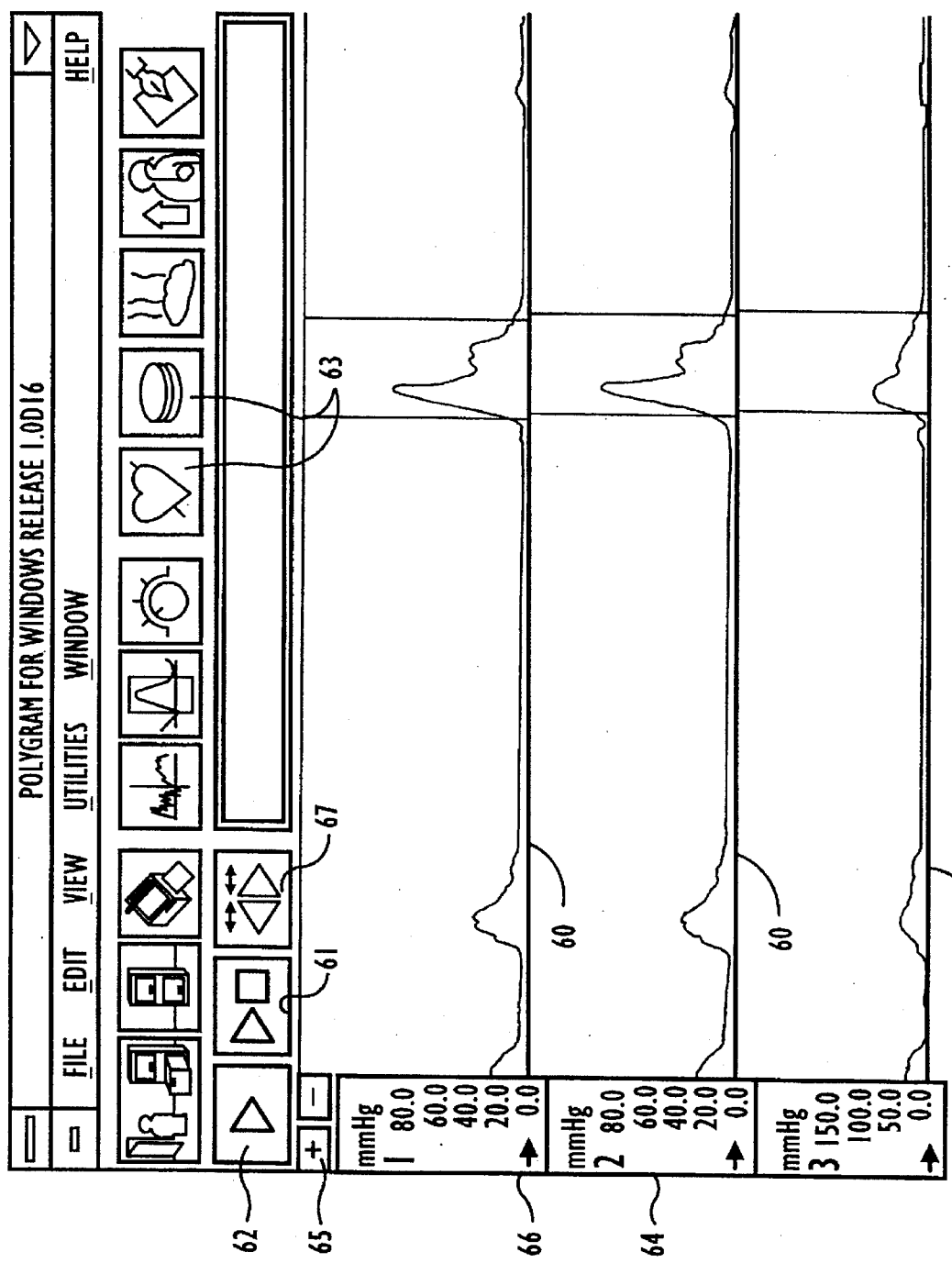
FIG. 12 shows the Perform Procedure screen of the software in accordance with the present invention.

Once a patient or patient group is selected and a Study is be carried out said Study is selected from the list of available Studies in the Study Name box 55. To register a patient is an example of a Study and said Study may be named Demographics 56. If the Study Demographics is selected, a Registration Form, FIG. 11, is displayed into which demographic data can be filled in. When a Study is selected, a list of its Procedures is presented if more than one Procedure is included. When a procedure is selected the Perform Screen FIG. 12 is shown on the computer. A number of tracings 60 corresponding to the parameters to be measured are passed by. With icon 61 the tracings are saved into memory. The icon changes and the next time it is clicked, the savings status is interrupted. With icon 62 any screen is momentarily frozen while recording, with or without the saving on feature continued in the background.

The screen can be divided in two parts. One with compressed tracing in a history window. Here it is possible to do tasks such as review, move around, expand, and search in the history window while the other window continuously displays realtime acquisition data.

In perform mode it is possible to mark segments as Events. It is also possible to insert markers 63 into the recording by clicking on one of the icons. It is possible to typewrite messages into the recording in a marker.

By double clicking on a channel in the channel header 64 said channel disappears. By clicking at the top or bottom + or − signs 65, said scale or offset change respectively.

Figure 13:
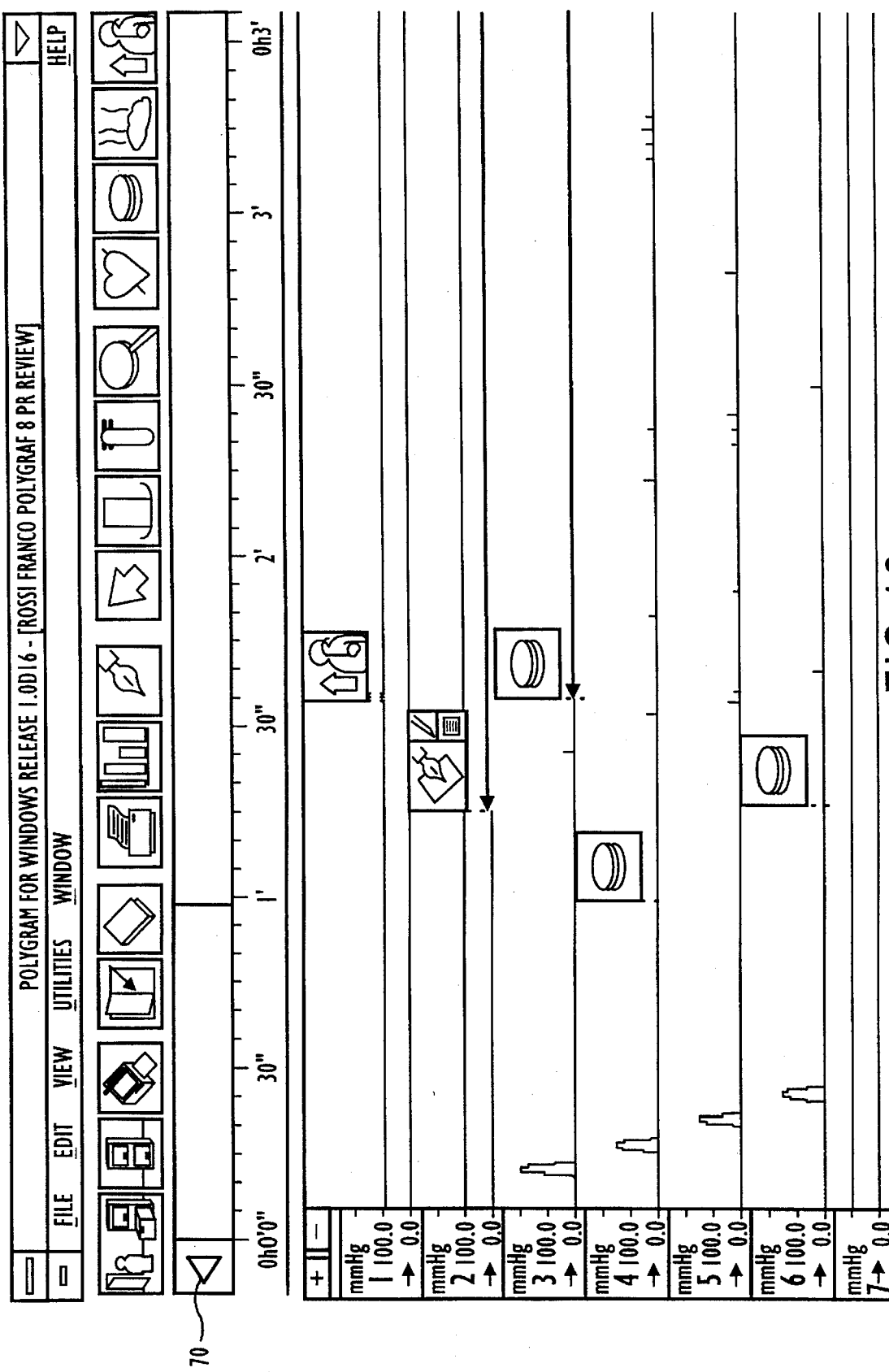
FIG. 13 shows the Review screen of the software in accordance with the present invention.
Figure 14:
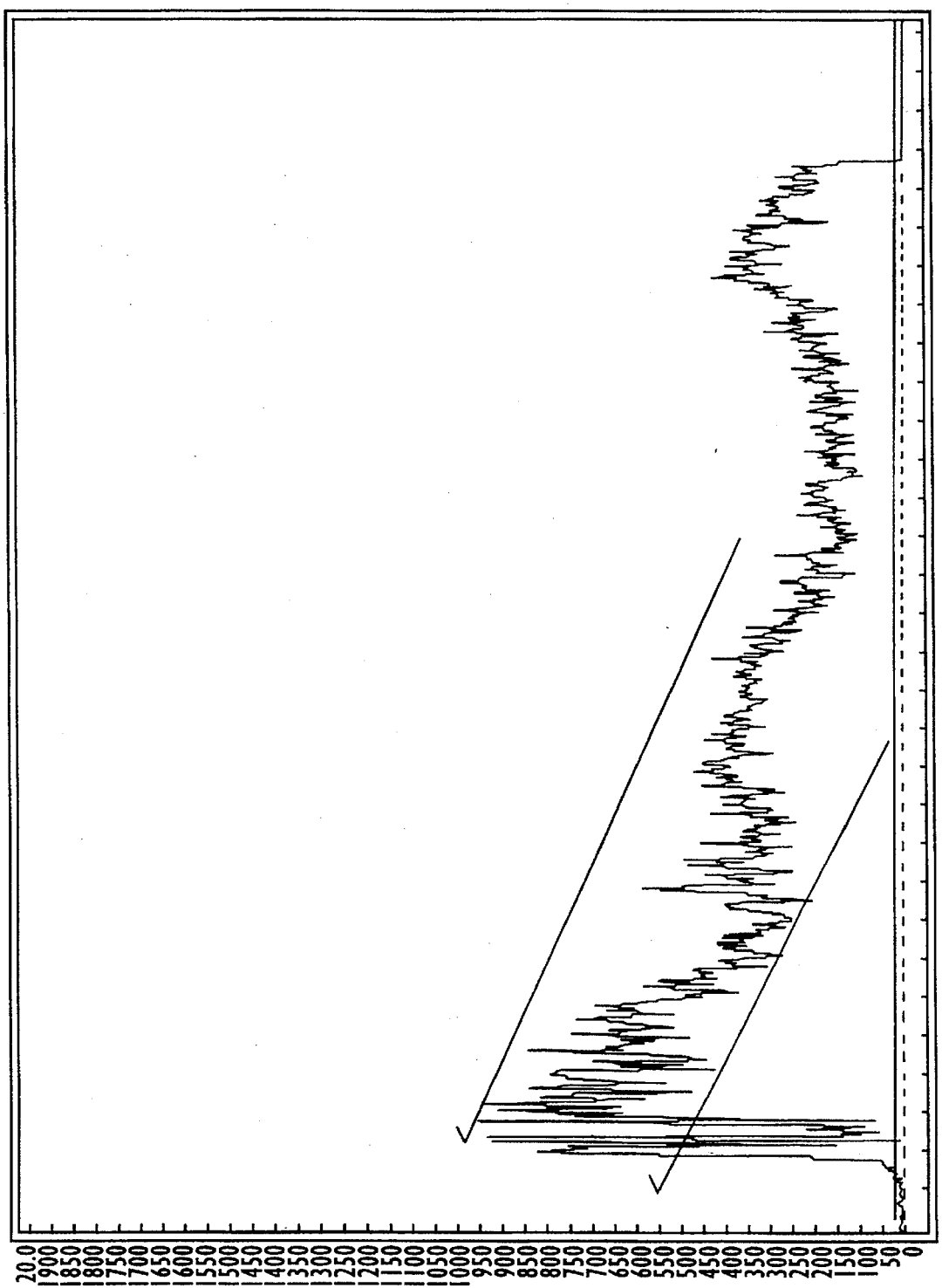
FIG. 14 shows a Gastric Emptying report with lines describing normality in accordance with the present invention.

When a Procedure is performed, the user clicks the stop button 61. To review the procedure, the user clicks icon 67. The Review screen is shown in FIG. 13. With a scroll bar 70 it is possible to address any part of the recording. The x-axis of the recording can be compressed or expanded. The markers and Events are displayed. In FIG. 14 a Gastric Emptying Tracing is displayed at compression rate 64. Distance between vertical lines is 5.0 minutes. The vertical scale is in units of counts per second.

The embodiment illustrated and discussed in this specification is intended only to teach those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

I claim:

1. A catheter comprising:
   (a) an ambulatory intragastrointestinal catheter with a tubular body having a distal end and a proximal end,
   (b) a first isotope activity sensor, having a distal end and a proximal end, in the distal end of said body,
   (c) a first gold shield at the distal end of the first sensor,
   (d) a second gold shield at the proximal end of the first sensor, and
   (e) an electrical conductor connected to said first sensor and running through an interior of said body, for the length of said body, to the proximal end of said body.

2. The invention of claim 1, wherein the first sensor further comprises a CdTe sensor element.

3. The invention of claim 1, wherein the electrical conductor further comprises a shielded cable.

4. The invention of claim 1, further comprising:

(a) a second isotope activity sensor, located adjacent to the first isotope activity sensor in the body and between the first gold shield and the second gold shield, the second sensor including means for sensing a type of isotope different from a type sensed by the first sensor, and (b) an electrical conductor connected to the second sensor and running through the interior of the body, for the length of the body, to the proximal end of the body.

5. The invention of claim 4, further comprising:

(a) a third isotope activity sensor, at a location in the body not adjacent to the first sensor, the third sensor having a distal end and a proximal end and including means for sensing the same type of isotope as the first sensor, (b) a third gold shield at the distal end of the third sensor, (c) a fourth gold shield at the proximal end of the third sensor, and (d) an electrical conductor connected to the third sensor and running through the interior of the body, for the length of the body, to the proximal end of the body.

6. The invention of claim 1, further comprising:

(a) an additional sensor attached to the body and selected from a group of sensors sensing, respectively, one of the following parameters:
pH,
impedance,
IGG,
EGG,
pressure, and
bile, and (b) an electrical conductor connected to said additional sensor and running through the interior of said body to the proximal end of said body.

7. The invention of claim 1, further comprising:

(a) a perfusion lumen having a distal end and a proximal end and extending through the length of said body, with an outlet hole through the body communicating between an exterior of the body and the lumen, the hole located near the distal end of said body, and (b) a connector at the proximal end of said lumen adapted for connection to a perfusion pump and pressure transducer.

* * * * *